United States Patent [19]
Caldarise et al.

[11] Patent Number: 5,687,788
[45] Date of Patent: *Nov. 18, 1997

[54] IMPLANTABLE ARTICLES WITH AS-CAST MACROTEXTURED SURFACE REGIONS AND METHOD OF MANUFACTURING THE SAME

[75] Inventors: Salvatore Caldarise, Hanson; Richard P. Manginelli, Milton, both of Mass.; David L. LaSalle, Woonsocket, R.I.; Timothy M. Flynn, Norton, Mass.

[73] Assignee: Johnson & Johnson Professional, Inc., Raynham, Mass.

[*] Notice: The term of this patent shall not extend beyond the expiration date of Pat. No. 5,662,158.

[21] Appl. No.: 457,227

[22] Filed: Jun. 1, 1995

Related U.S. Application Data

[62] Division of Ser. No. 198,874, Feb. 18, 1994, abandoned.

[51] Int. Cl.$^6$ .................................................. B27C 9/00
[52] U.S. Cl. ........................... 164/456; 164/4.1; 164/6; 164/526; 164/528
[58] Field of Search ........................ 164/4.1, 6, 525, 164/526, 527, 528, 529, 456

[56] References Cited

U.S. PATENT DOCUMENTS

| | | | |
|---|---|---|---|
| 4,330,891 | 5/1982 | Branemark et al. | 3/1 |
| 4,355,428 | 10/1982 | Deloison et al. | 3/1.91 |
| 4,479,271 | 10/1984 | Bolesky et al. | 3/1.911 |
| 4,608,052 | 8/1986 | Van Kampen et al. | 623/22 |
| 4,828,563 | 5/1989 | Müller-Lierheim | 623/16 |
| 4,863,474 | 9/1989 | Brown et al. | 623/16 |
| 4,865,608 | 9/1989 | Brooker, Jr. | 623/23 |
| 4,878,914 | 11/1989 | Miwa et al. | 623/16 |
| 5,002,575 | 3/1991 | Johnson | 623/16 |
| 5,108,435 | 4/1992 | Gustavson et al. | 623/16 |
| 5,133,770 | 7/1992 | Zweymuller et al. | 623/16 |
| 5,178,201 | 1/1993 | Ahlers | 623/16 |
| 5,204,055 | 4/1993 | Sachs et al. | 419/2 |
| 5,207,709 | 5/1993 | Picha | 623/11 |
| 5,236,457 | 8/1993 | Devanathan | 623/16 |
| 5,524,695 | 6/1996 | Schwartz | 164/34 |

FOREIGN PATENT DOCUMENTS

| | | | |
|---|---|---|---|
| 380687 | 9/1989 | Germany | 164/35 |
| WO 92/21302 | 12/1992 | WIPO | 623/11 |
| WO 93/07835 | 4/1993 | WIPO | |

*Primary Examiner*—Kuang Y. Lin
*Attorney, Agent, or Firm*—Nutter, McClennen & Fish, LLP

[57] ABSTRACT

An implantable article having on at least a portion of its exterior surface an integral, as-cast macrotextured surface with macropores having undercut edge profiles. A complex macrotextured surface is provided by forming a casting mold so that the mold has complementary macrotextured surface features formed by three-dimensional printing techniques, and casting a molten metal within or in contact with the casting mold to form the implantable article. In a hybrid process, one or more printed surface mold plates are attached by hand, or in a wax molding process, to a simpler wax preform, and an investment is made in which the plates are incorporated into the investment mold. A casting is then made, with each preform yielding one cast article, and the incorporated plate forming the desired surface macrotexture on a region of the east article. Pore size, porosity and pore shape may be varied across the surface, or varied with depth, to independently enhance different mechanical and physiological factors at the bone-prosthesis interface.

9 Claims, 6 Drawing Sheets

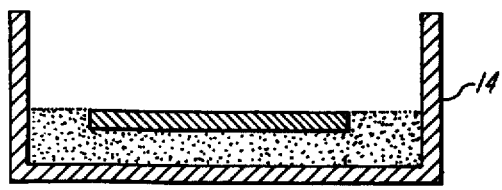
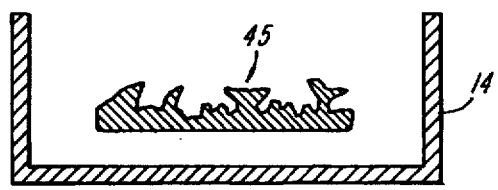
*FIG. 4A*  *FIG. 4B*
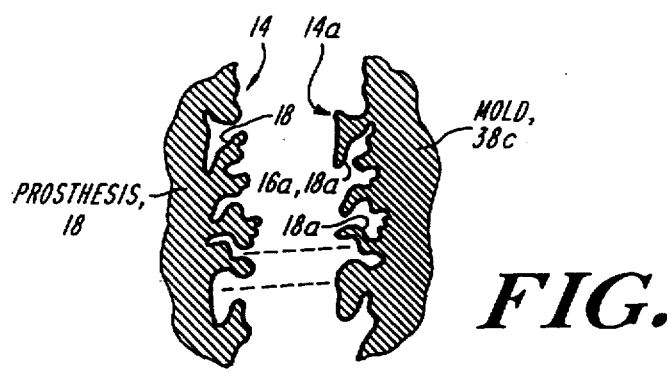
*FIG. 5*
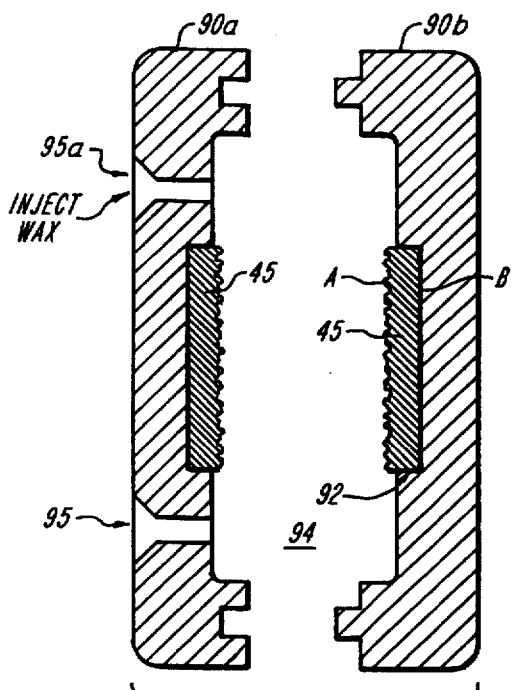
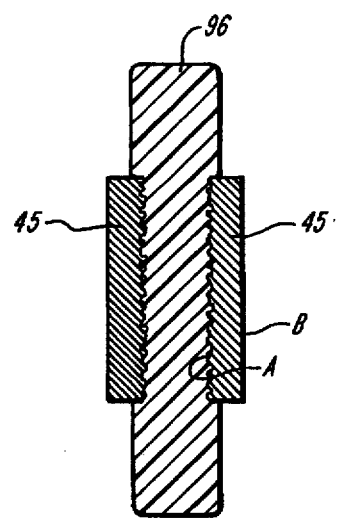
*FIG. 6B*  *FIG. 6C*

IMPLANTABLE ARTICLES WITH AS-CAST MACROTEXTURED SURFACE REGIONS AND METHOD OF MANUFACTURING THE SAME

This is a divisional of application Ser. No. 08/198,874 filed on Feb. 18, 1994, now abandoned.

This application is related to U.S. patent application Ser. No. 08/198,607, filed concurrently herewith by the same inventors and entitled "BONE PROSTHESIS WITH DIRECT CAST MACROTEXTURED SURFACE REGIONS AND METHOD OF MANUFACTURING THE SAME", which application is hereby incorporated by reference.

BACKGROUND OF THE INVENTION

The invention relates to implantable articles and methods for manufacturing such articles. More particularly, the invention relates to bone prostheses and casting processes for manufacturing the same.

There are known to exist many designs for and methods for manufacturing implantable articles, such as bone prostheses. Such bone prostheses include components of artificial joints, such as elbows, hips, knees, and shoulders. An important consideration in the design and manufacture of virtually any implantable bone prosthesis is that the prosthesis have adequate fixation when implanted within the body.

Early designs of implantable articles relied upon the use of cements such as polymethylmethacrylate to anchor the implant. The use of such cements can have some advantages, such as providing an immediate and secure fixation that does not develop free play and lead to erosion of the joining bone faces post-operatively. However, the current trend is to use these cements to a lesser extent because of their tendency to lose adhesive properties over time and the possibility that the cements contribute to wear debris within a joint.

Recently, implantable bone prostheses have been designed such that they encourage the growth of hard tissue (i.e., bone) around the implant. Bone attachment usually occurs and growth is promoted where the surface of an implantable bone prosthesis is irregular or textured. The interaction of newly formed hard tissue in and around the textured surface of the implantable bone prosthesis has been found to provide good fixation of the prosthesis within the body. A greater degree of bone fixation can usually be achieved where bone engaging surfaces of an implantable bone prosthesis are more porous or irregular.

Porous or irregular surfaces can be provided in implantable articles by a variety of techniques. In some instances an irregular surface pattern or surface porosity is formed in an implantable bone prosthesis by embossing, chemical etching, milling or machining. One drawback to using such techniques to provide irregular bone ingrowth surfaces in implantable bone prostheses is the significant amount of post-processing time required. The post-processing operations lead to delays in obtaining the finished product and also significantly increase the cost of manufacturing the device. These post-processing operations can also diminish the mechanical properties of the device.

Textured surfaces are also applied to implantable bone prostheses by joining one or more separate surface plate inserts to an exterior surface of the prosthesis to provide separate porous surfaces or pore-forming surfaces. Separate, pore-forming surfaces can be joined to or formed on an implantable bone prosthesis by sintering small metal particles or powders to a surface of the prosthesis in a random pattern. Wire-based pads or grids can also be fused to implantable bone prostheses to provide a texture or surface relief features. A drawback of such techniques is that the components added to form the textured surface can become dislodged from the prosthesis. Dislodgment of these components compromises the fixation mechanics of the implant and can also contribute to wear debris. Further, the sintering step required to fuse texture-forming components to bone prostheses is a high-temperature post-processing step that could impart mechanical weaknesses to the prosthesis, distort the dimensions of the prosthesis, and/or alter the properties of the materials from which the prosthesis is made.

Optimal bone fixation is believed to occur with implants that have more complex and irregular surfaces on a rather small dimensional scale, which provides a larger bone-engaging surface area with some depth of texture. Apparently, hard tissue (i.e., bone) is able to infiltrate small pores and passages that form the textured surface, thus providing firm interlock between the implant and the bone. It is also believed that the best textured surfaces for implantable bone prostheses are those in which the macroporous surface is integral with the prosthesis, as opposed to macroporous surfaces that are separately fused to the prosthesis by post-processing operations.

It is believed that an ideal textured surface would be one in which the macroporous textured region of an as-east article includes macropores with undercut edge profiles. Unfortunately, available technology has not previously enabled the manufacture of implantable articles with such macroporous surfaces.

Implantable articles such as bone prostheses are often made by an investment casting process. Investment casting first requires the manufacture of a solid model of the article to be cast. The solid model is usually made from a meltable casting wax through a molding operation such as injection molding. Once the solid model is made, one or more of the solid models are fixed to a wax tree which is then encased, along with the attached solid models, in a refractory binder material. This is done by repeatedly dipping the assembly in a ceramic slurry coating and drying the coating between dips, to form a shell. After final drying, the shell is heated to a temperature sufficient to melt and extract the casting wax from within the shell. Thereafter, the shell may be sintered or fired at a higher temperature, that also burns off any residues. Molten metal is then poured into the investment assembly to entirely fill the cavities once occupied by the solid models and form cast articles having the shape of the hollow regions left by the lost wax.

Although it is known to be useful to form implantable bone prostheses having as-cast macroporous textures, it is difficult to do so using the traditional investment casting techniques described above. The first step, requiring preparation of solid models by molding poses a serious limitation of such a process. It is difficult, if not impossible, to incorporate suitable macrotextured surface into a solid model formed by an injection molding process because release of the model from the mold becomes more difficult with increasing surface complexity, and may destroy the model. If the model has undercut surface features, it cannot be separated from the mold without breaking either the model, the mold, or both.

Accordingly, there is a need for bone prostheses having improved textured surface characteristics that enhance the fixation mechanics of the implantable prostheses to hard tissue within the body. There is also a need for improved methods of manufacturing prostheses having such characteristics.

It is thus an object of the invention to provide implantable articles such as implantable bone prostheses having surface characteristics that promote hard tissue ingrowth and improved fixation within the body.

It is also an object of the invention to provide implantable bone prostheses having exterior, bone-engaging surfaces that include an as-cast, macrotextured region.

Another object of the invention is to provide casting techniques that enable the manufacture of implantable bone prostheses having as-cast macroporous textured surfaces.

A further object of the invention is to provide casting techniques that facilitate the manufacture of implantable bone prostheses with as-cast macrotextured surfaces designed to take advantage of optimum fixation mechanics for a given prosthesis. These and other objects will be apparent from the description that follows.

SUMMARY OF THE INVENTION

These and other objects are achieved in a bone prosthesis and a method of making the prosthesis, wherein at least a portion of the prosthesis has an cast surface texture of intact features defining macropores. Preferably, the macropores are undercut, or extend, at least in part, in a direction other than perfectly normal to the surface. The process includes the steps of manufacturing a mold surface, which may be a vase-like enclosure constituting the entire mold or may be a small plate or shell, by building the surface up in layers. A powder material of suitable composition is laid down layer by layer, and a portion of each layer is solidified by applying a binder material in selected regions thereof. In this manner a green mold is then dried and fired, and a solid bone prosthesis is formed by filling the mold with casting material such as metal or metal alloy. The spent mold is separated from the cast prosthesis by mechanical and chemical means, leaving a solid prosthesis in which complex surface features have been directly formed by the casting process.

Open and closed mold surfaces are printed by an imagewise deposition of binder material, wherein a computer controlled scanner and feed mechanism defines a macrotextured surface. Textures of loops, hooks, ridges, pits, posts and tunnels can be formed in large patterns or repetitive arrays on the mold surfaces so printed, as well as on the cast article of complementary surface shape. Different ceramic-forming powder materials as well as binders may be used to build ceramic molds or to form ceramic plates for insertion into ceramic molds, in which high temperature alloys are cast. Modified lost wax processes allow the use or mass molding of featureless wax preforms with printed texture plates, or connected arrays of printed molds to efficiently cast many prostheses at once.

BRIEF DESCRIPTION OF THE DRAWINGS

FIGS. 4A and 4B illustrate the manufacture of a textured mold insert for making an implantable article according to another method of the invention;

FIG. 5 is an enlarged sectional view of a mold and corresponding portion of a cast prosthesis of the invention;

FIGS. 6B and 6C illustrate an alternative process using the insert of FIG. 4A;

DETAILED DESCRIPTION OF THE INVENTION

The present invention relates to implantable articles such as bone prostheses that have a bone-engaging surface bearing an integral, as-cast macrotextured surface over at least a portion thereof.

Figure 1A:
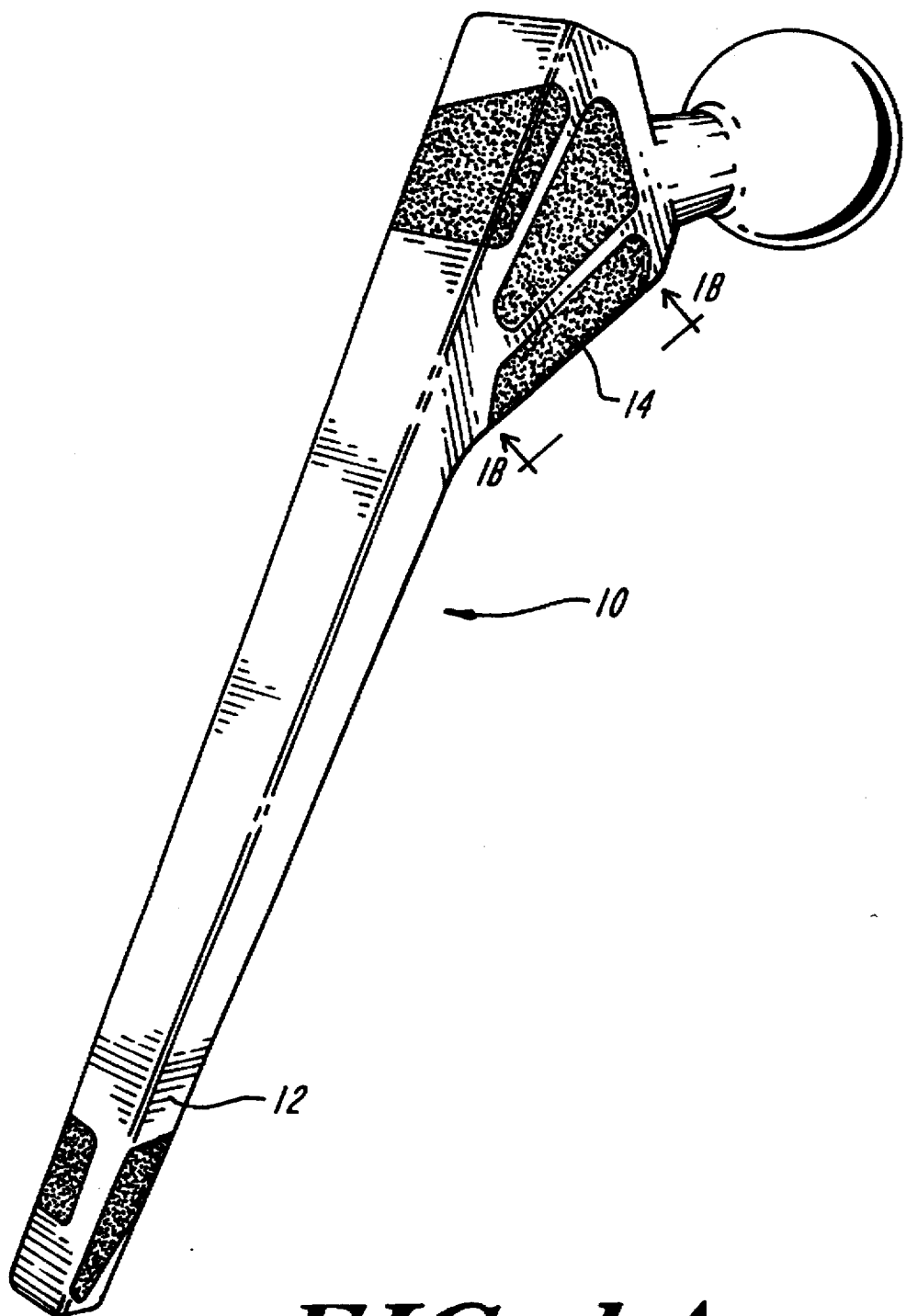
FIG. 1A is a side perspective view of a femoral stem for a human hip prosthesis.
Figure 1B:
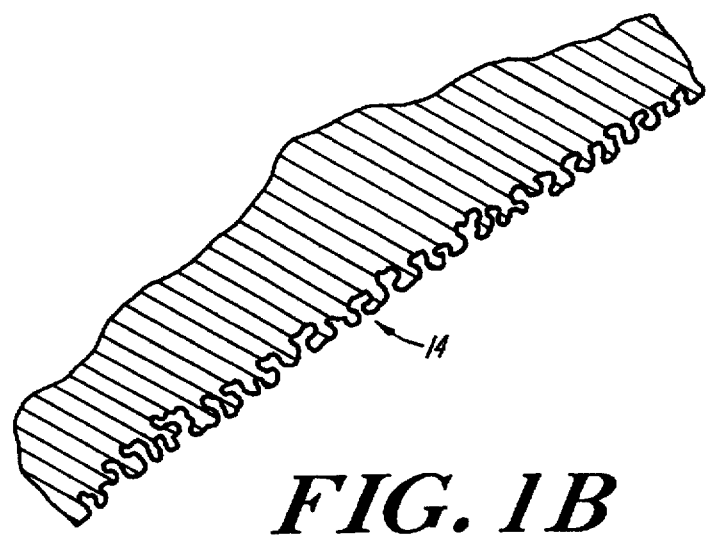
FIG. 1B is a section detail of the stem of FIG. 1A illustrating in greater detail an as-cast macrotextured surface.
Figure 2A:
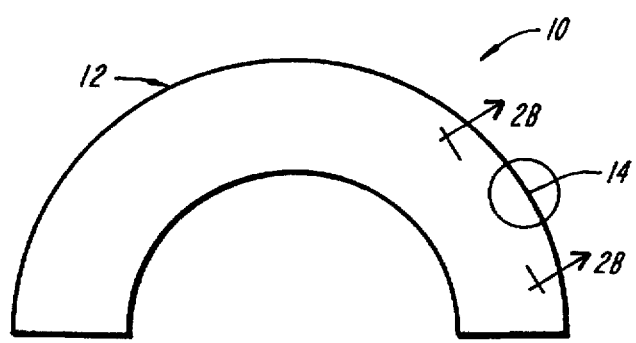
FIG. 2A is a view of an acetabular shell for a human hip prosthesis.
Figure 2B:
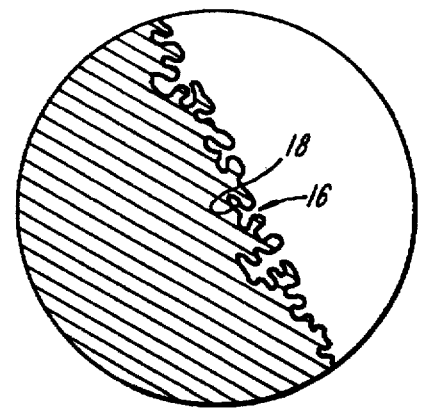
FIG. 2B is a section view of the shell of FIG. 2A illustrating in greater detail an as-cast macrotextured surface.

Two representative implantable bone prostheses 10 of the present invention are shown in FIGS. 1A and 2A. The embodiment of FIG. 1A is a hip femoral component of a human artificial hip joint. The embodiment of FIG. 2A is an acetabular shell component of a human artificial hip joint. Sectional views FIGS. 1B and 2B illustrate in enlarged detail a representative macrotextured surface portion of each implant 10 and undercut edge profiles thereon.

The term "macrotextured", as used herein, refers to a textured surface which has surface features, for example, pores or voids, ranging in size from approximately 150 to 600 micrometers in diameter. This size range corresponds roughly to the particle size of a medium sand, on the fine end, to a medium coarse sand on the large end. The term "undercut edge profiles", as used herein, refers to the geometry of the macrotextured surface wherein the dimensions, or profile of the macrotextured surface structures as measured in a plane parallel to the nominal surface of the prosthesis, extend further, at least in one direction, with increasing distance away from the surface; or viewed in the larger sense, wherein undercuts or horizontal cavities are formed in features that extend outward from the surface. This description should be qualified, however, in that the dimensions need not yield successively surface greater areas in each plane, but only that at the edge between a solid surface and an adjacent pore or void, the solid surface extends over the void with increasing height, or lies above or overhangs the void. Viewed from above the surface, such features would include file-like tooth protrusions with a negative rake angle, as well as other vertical protrusions having an inward slant, and would also include protruding or indented walls with a horizontally-aimed indentation or tunnel below the top of the wall.

The macrotextured surface of the prosthesis is comprised of pores having an approximate "diameter" or feature size, of between 150 and 600 micrometers. A preferred pore size for optimum hard tissue ingrowth is between approximately 250 and 300 micrometers in diameter. A preferred range of porosity, or total void region of the macrotextured surface as seen in a section parallel to the surface, is approximately thirty to sixty per cent. The undercuts of the pores preferably have a depth of from approximately one-half to about one-and-a-half millimeters. Thus, the pores are relatively deep invaginations in the surface profile, relative to their in-plane dimensions, being one to three times as deep as their horizontal extent.

As illustrated in FIGS. 1 and 2, the implantable bone prosthesis of the present invention comprises an implantable article 10 which has an outer bone-engaging surface 12. At least a portion 14 of the bone-engaging surface 12 bears an integral, as-cast macrotextured surface which includes pores 16 having undercut edge profiles 18.

The implantable articles of the present invention, while not limited to a particular design, may be any one of a number of bone prostheses. Such prostheses include, but are not limited to spinal implants, a femoral stem for an artificial hip, an acetabular shell or component thereof, a tibial plateau for an artificial knee, or a femoral component thereof. A substantial portion oft he outer surfaces of these prosthetic devices is comprised of bone-engaging surfaces. That is, the device contains surface regions in which trabecular bone growth is promoted, so that the device becomes firmly attached to new hard bone by natural growth processes. The incorporation of the integral, as-cast macrotextured surface of the claimed invention in these regions is intended to provide improved fixation of these devices to the surrounding bone.

As indicated above, the depth-to-diameter ratio of the preferred surface pores achieved by the invention is relatively large, approximately unity to about three. In practice, the provision of a rough surface with deep relief allows bone debris created during the initial fitting of the prosthetic surface against adjacent bone to fall or be packed into the pores, creating a good environment for and promoting subsequent trabecular bone growth. Once ingrown with bone, this would not only fix the device, but behave as a seal preventing wear debris from migrating. The presence of undercutting provides a relatively larger volume below the contact surface. This provides a relatively larger area of surface contact at the outer surface for load bearing and coupling to natural bone, whereas without undercutting, a large contact surface could only be obtained at the expense of pore volume. In addition, by providing undercuts in the prosthesis, new bone growth "dovetails" where it joins the surface, providing absolute rigidity of coupling against tensile forces acting in three axes. All of these features are expected to enhance the strength and lifetime of the joint.

As previously discussed, the direct creation of surface porosity on a bone prosthesis can pose numerous manufacturing problems. Typically, a prosthesis is made of a strong material, such as a east metal, which is formed at a high temperature. While such items might readily be formed by investment casting from a wax model, with subsequent destruction of the investment or casting mold, the production of an original wax model having such surface topography poses some difficulty since there appears to be no way to mass produce the positive pattern with a complex surface topography.

This problem is overcome in accordance with one aspect of the present invention by novel processes for manufacturing articles such as prostheses having the surface relief features described herein. In particular, a novel method for making an implantable bone prosthesis having an integral, as-cast macrotextured surface, employs a computer-controlled three-dimensional printing technique to build a casting mold for directly casting the desired prosthesis. The casting mold, or a separate plate for incorporation into the mold to define a pattern-forming surface thereof, is built up of loose powder applied in successive layers, with a binder selectively applied at each layer, by a computer-controlled scanning nozzle similar to an ink jet, to selectively solidify the powder in each layer in a region or profile corresponding to the section of the desired three-dimensional solid.

Suitable three-dimensional priming techniques for the practice of the invention are disclosed in U.S. Pat. No. 5,204,055 to Sachs et al., which patent is hereby expressly incorporated herein by reference. In accordance with the present invention, using specialized three-dimensional powder printing patterns, investment casting molds or mold lining plates with macroporous textured surfaces having undercut edge profiles and other complex texture features are manufactured.

The process involves the deposition of a layer of a powder material in a confined area and the application of a binding material to selected regions of the powder layer to solidify it in those regions. A next layer of powder is then deposited over the first layer, and binding material is again applied to selected, generally partially overlapping, regions of the second layer of powder to solidify it in those new regions and bind the solidified sections to the previously solidified sections of the layer below. These steps are repeated according to a predetermined pattern to obtain an object formed of many successive laminations of powder and binding material. The regions in which binder material is deposited in each scan layer correspond to the sections, at the current scan height, of the three-dimensional object being formed. As described further below, this object preferably comprises all or part of a mold surface, which may be either an open or a closed mold surface. By "closed" is meant a cup-shaped cavity, into which a complementary-shaped article may be directly cast. By "open" is meant a curved or flat plate which is not intended, in and of itself, to receive a casting medium, but which may be incorporated into other bounding surfaces to form a mold cavity and impart a desired shape to an object cast therein.

In accordance with the present invention, detailed relief structures are built into the mold surface to form macropores with desired edge characteristics in the article of complementary shape, formed by molding in contact with the mold surface. A broad range of contour, shape or surface texture may thus be imparted to the cast article. In practice, the extent of detail and complexity which can be attained in objects manufactured using three-dimensional printing processes is limited by the resolution of the binder application mechanism that applies the binding material to the powder layer to form detailed or complex patterns. Because three-dimensional printing processes are generally computer controlled, virtually any design which can be scanned or interpreted by a computer may be reproduced, regardless of its complexity, subject to the resolution limit. Resolution for the powder consolidation three-dimensional printing discussed below readily attains a feature size below 0.2 millimeters, and is subject to improvement with adjustment of the layer thickness, scan nozzle geometry, powder size and binder viscosity and wetting properties, as will be appreciated by those familiar with this process.

Figure 3A:
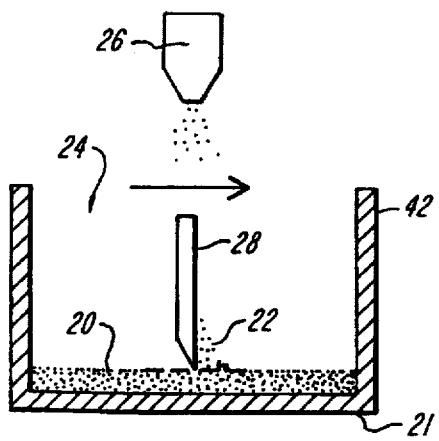
FIGS. 3A-3E illustrate the sequence of steps in one method of making a casting mold for an implantable article according to the invention.

A method of making a bone prosthesis according to the invention is illustrated in FIGS. 3A–3E. The process begins with the deposition of a layer 20 of powder material 22 in a confined region 24, as shown in FIG. 3A. The confined region is defined on the surface of a stage or platen 21 which is movable in a feed direction, indicated by axis Z, perpendicular to the plane of the platen. Motion along the feed direction allows the platen either to receive additional layers of powder material or to permit removal of the finished part. The powder material is deposited in a very thin layer within a contour in the confined region which is preferably selected to encompass either a longitudinal or transverse cross-sectional profile of a mold for forming the desired bone prosthesis. Each layer of powder material is preferably not more than approximately one or two hundred micrometers deep and the powder is sprinkled so it is relatively loosely spread, from a powder dispensing mechanism 26 located over the confined region. A doctor blade 28, a sonic vibrator or other leveling device is passed over the powder layer or is otherwise activated to smooth out the layer and assure that the layer has uniform thickness.

The powder material may be any material which is capable of being solidified upon the application of a binder and of forming a casting mold. Typical powder materials used in the method of the invention are ceramic-forming materials, such as alumina, beryllia, silica, silicon carbide, zirconia powders, and other materials and mixtures thereof, possibly with materials that may act as fluxes or mold conditioners, such as are generally employed in making ceramic molds or in investment casting.

Figure 3B:
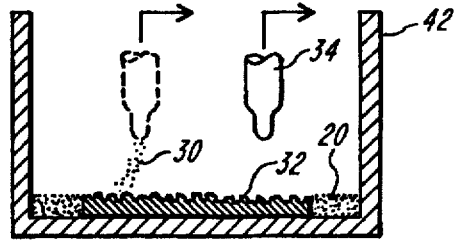
Figure 3C:
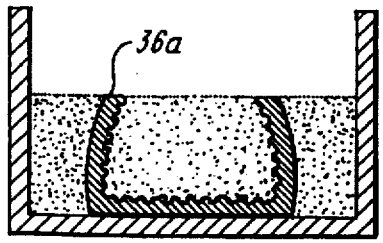
Figure 3D:
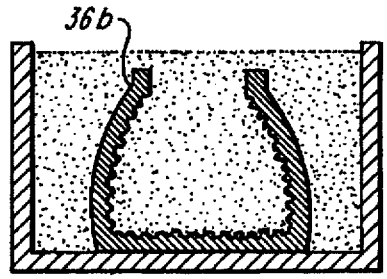

As shown in FIG. 3B, after deposition of a uniform unconsolidated powder layer 20, a binding material 30 is deposited onto selected regions 32 of the powder layer 20 according to a pattern which is defined by the desired cross-sectional dimensions of the bone prosthesis at the given location and the surface features to be imparted to the prosthesis. It is preferred to dispense the binding material 30 from a deposition mechanism 34, that operates like an ink-jet print head, which has relatively fine resolution, appropriate to the level complexity and dimensional detail to be attained in the resulting cast article. The mechanism 34 is preferably controllably scanned, e.g., by appropriate carriage and stepper drive, over the powder area to define an image-wise pattern 32 of binding material 30. As with conventional image-printing techniques, the mechanism 34 may include means for adding a micro-deflection or offset to the liquid nozzle so as to effectively print with half-dot resolution.

The binding material 30 may be any organic or inorganic binder material which will wet or react with, and solidify or fix the position of the powder material to which it is applied. Typical binding materials may include cellulosic and butyral resins, polycarbosilazane and silicate-based materials, aqueous or alcohol based colloidal silica and other preparations normally used as binders for forming ceramic molds. Aqueous colloidal silica is the presently preferred binding material when the material is used to form the powder layer is to be fired into a solid ceramic.

The powder deposition and binding material application steps of FIGS. 3A and 3B are repeated as each powder layer is solidified in the selected regions according to the predetermined scan actuation pattern. With each scan, the platen 21 is moved along the Z axis perpendicular to the plane of the platen a distance equal to the thickness of the powder layer 20 to permit the deposition of a new powder layer and the application of binding material to the new layer. The solidified sections of each successive powder layer are bonded to at least a portion of the solidified regions in the powder layer immediately below, so that the entire multi-layer deposition and scan process defines a single continuous three-dimensional object composed of numerous thin ring-like slices of powder material solidified and bonded together with each other by the binding material into a solid shell.

In this manner, a complete mold 36b (FIG. 3D) or partial mold surface 36a (FIG. 3C) is built up. For example, using alumina powder for the layers 20 and colloidal silica for the pattern solidifying binder material, a green (i.e., unfired) casting mold is built up to define a vase-like vessel or cavity 38 in which the bone prosthesis may be formed. The casting mold or surface is thus a negative of the bone prosthesis in the sense that it is the spatial complement of, and it defines the outer contours and surface textures of the prosthesis. As illustrated by the enlarged detail, FIG. 5, at least a portion (38C, FIG. 3E) of the interior or article-contacting surface of the casting mold 38 bears a macroporous textured surface 14a with macropores 16a having undercut edge profiles 18a which are the spatial complements of elements 14, 16 and 18 shown in FIGS. 1A and 2A. When the casting mold is filled with molten metal to form the prosthesis, the exterior surfaces of the bone prosthesis thus acquire the macroporous surface texture.

By employing three-dimensional printing techniques to make implantable articles, applicant is able to mass produce articles which have macroporous textured surfaces via the mass production of casting molds which have complex textures including complementary macropores with undercut edge profiles. The casting molds are mass produced directly out of ceramic materials, with the casting mold constructed layer by layer in a three-dimensional printing process, so there is no need to make a solid model of the desired object (which would be damaged upon release from a mold). The printed mold of FIGS. 3–5 is used to cast a metal prosthesis and the mold may be removed from the prosthesis without damaging the cast metal prosthesis. For example, ultrasonic fracturing and solvent removal may be used to selectively remove the ceramic material without attacking the attached molded metal article. This assures that there is no risk to the delicate and/or complex surface geometries on the molded object. Thus, rather than attempting to make wax models of the desired prosthesis shape, the present invention starts with an automated process to mass produce complex but disposable single use molds for forming the prosthesis.

Once the mold form 38 is printed (FIGS. 3A–3E, or FIGS. 4A, 4B), loose powder material 22 which is not solidified or bonded within the casting mold is removed from the casting mold. The mold may be shaken to dislodge and remove the loose powder, or it may be immersed in a bath or solvent in which the loose powder material is washed away or dissolved while the solidified portions of the mold remain. Loose powder material which is difficult to remove completely because of its location within the casting mold may be more readily removed by subjecting the casting mold to ultrasound or other high-frequency vibration, followed by or concurrently with immersion in a bath or solvent. In some instances where the mold is created with complex macro-textured surfaces having undercut edge profiles, the particles of powder material and the macropores may be of a comparable size, resulting in at least partial blockage of the macropores. Ultrasonic vibration and/or immersion in a bath or solvent are particularly useful to remove the confined loose particles by dislodging and floating away the particles from the pores on the casting mold surfaces.

Figure 3E:
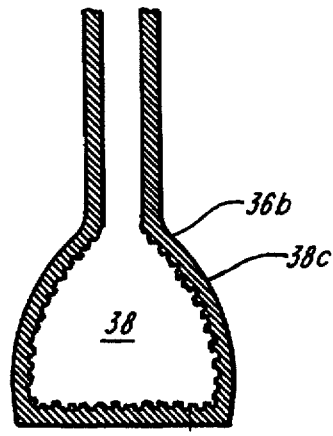

After the loose powder material is removed from the casting mold, the hollow casting mold FIG. 3E is preferably baked to drive off volatile material, and fired in a furnace at a suitable temperature for a suitable time to yield a strong ceramic mold. A preferred powder material for forming the mold is alumina which, when solidified with an application of aqueous colloidal silica as a binding material, may be fired at about 1925° F. for approximately two hours to form a fired alumina casting mold. The fired casting mold is extremely strong and thermally stable so that it defines a very precise mold cavity.

Depending on the degree of ceramic consolidation that is desired for proper mold strength, a certain amount of shrinkage may be expected on firing the green ceramic. Accordingly, those having ordinary skill in the art will readily appreciate that mold shrinkage can be compensated for by forming molds enlarged by a scale factor over the size of the article which is ultimately to be cast therein. With the materials described above, applicant has found shrinkage to be on the order of a few percent, or less.

After firing, the hollow mold 36 FIG. 3E receives a molten metal or metal alloy which is allowed to solidify to form the prosthesis 10. Suitable metal alloys include, but are not limited to, cobalt-chromium and titanium-vanadium alloys and those which are typically used in the manufacture of implantable prostheses.

Figure 6:
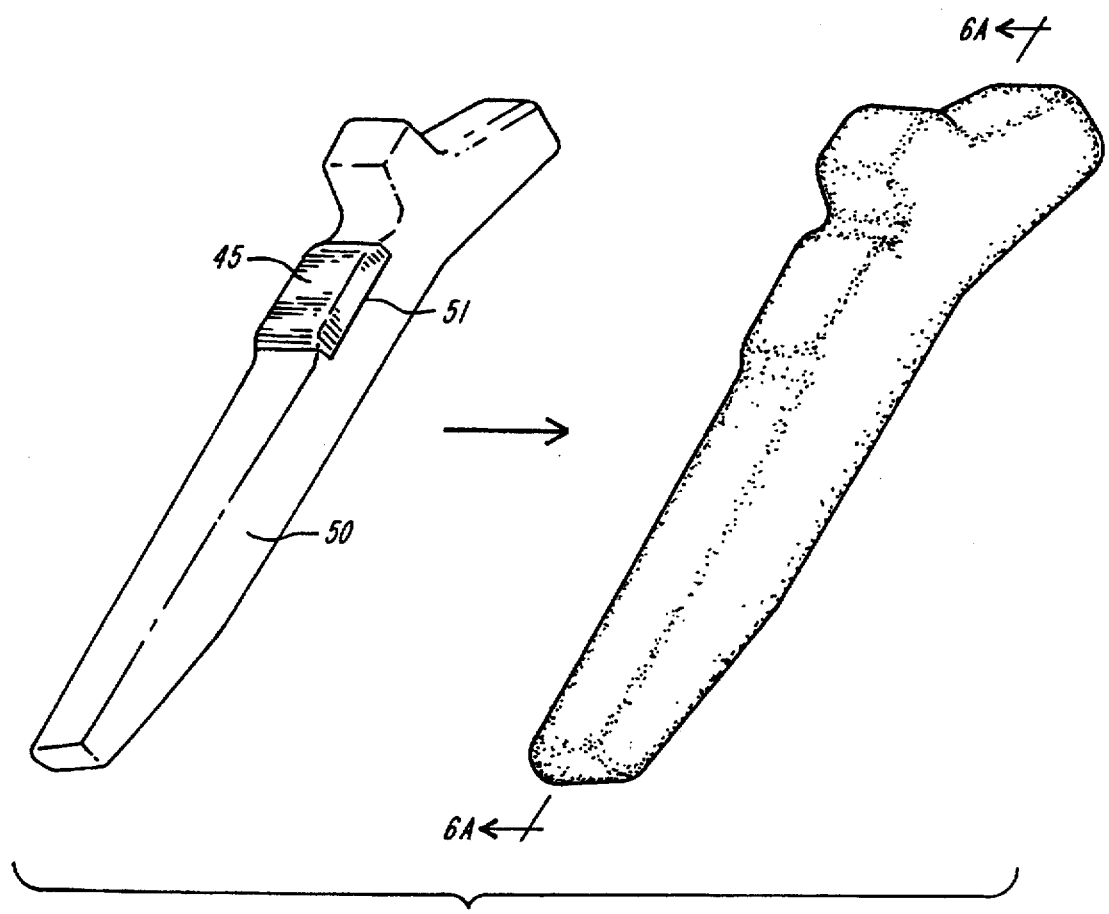
FIGS. 6 and 6A illustrate a casting process for a mold using the insert of FIG. 4A.
Figure 6A:
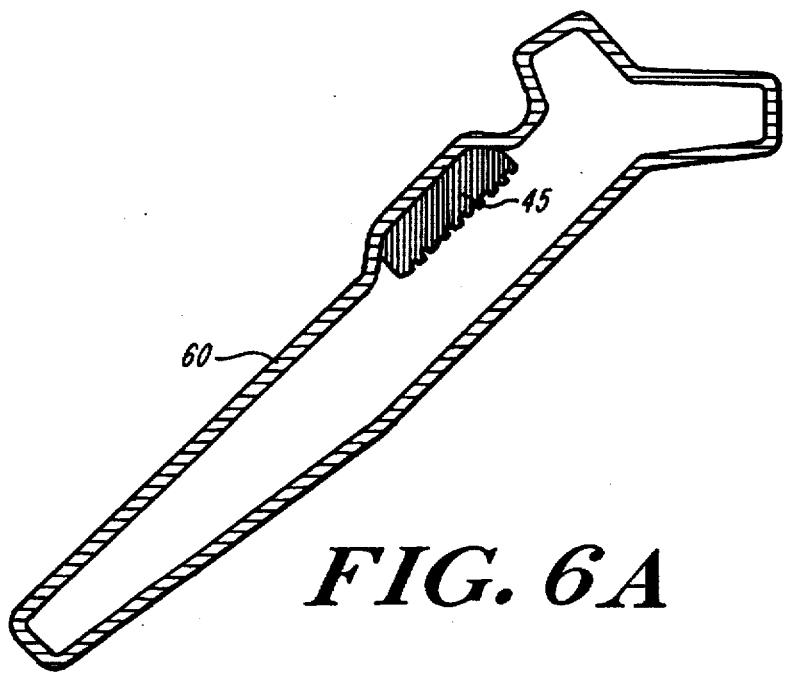

Alternatively, the same priming process may be used to form a separate texture plate 45 (FIGS. 4A and 4B) which is then incorporated into a conventional mold body to impart its surface texture to a bone prosthesis cast therein. FIG. 6 illustrates representative steps for forming a cast metal prosthesis in this fashion. A wax positive or preform 50 which has smooth or simple surface texture, is made by conventional techniques to serve as a shape for investment. Regions 51 of the perform, corresponding to the textured regions 14 of the final prosthesis, are originally smooth and flee of texture. In each such region 51, a mold plate 45 made as illustrated in FIGS. 4A and 4B is warmed and pressed, or otherwise attached to the perform 50 with its textured outer surface bearing against the wax of the perform, which thus holds the mold plates in position. The entire assembly is then dipped in a ceramic-forming slurry to build up an investment or easing 60 over the mold plate 45 and perform 50. The wax perform is driven off and a casting is made in the investment in a conventional manner.

When building texture plate 45 is incorporated into an investment in this manner, the plate may be installed green and may be fired with the investment so that it becomes integral therewith and the thermal properties of the plate and the investment match, and do not create undue stresses in the final fired ceramic mold. It will be understood that while one plate 45 is illustrated, many such plates may be attached to the preform, to form all the required areas of texture 14 illustrated in FIG. 1.

If desired, a plurality of casting molds so produced may be grouped in a cluster as is done with conventional investment casting. Wax rods can interconnect each perform to a central wax tree, and the whole assembly is refractory-coated to define a central channel connected to each casting mold by a runner system. The refractory coating material as just described for building a mold onto a texture plate 45, seals all the green casting molds together without diminishing the detail of the macrotextured structures formed thereon. The resulting refractory-encased cluster of casting molds is fired in an oven in one or more stages at suitable temperatures and times to remove the wax rod system and produce an interconnected cluster of fired casting molds. Molten metal is then cast into the duster of fired casting molds, entering the runners to fill the molds and form multiple prostheses with a single casting operation, each prosthesis having identical, integral, as-cast macrotextured surfaces complementary to those of the molds 38 or mold plates 45 described above.

In casting, various mold-filling techniques may be used to assure good surface penetration by the cast metal into the complex ceramic relief texture. This may be achieved by vacuum techniques, centrifugal casting, or by the provision of special gating configurations appropriate to the cast shape.

It should be understood that for some casting shapes, the process step of flowing molten metal into the mold may be replaced by a powder casting process, in which a metal powder fills the mold. In that case, heat is later applied to solidify the casting.

After casting, the prostheses 10 are then removed from the casting mold(s) as finished product. Where the casting mold is green (i.e., unfired), it is readily crumbled and destroyed and separated from the prosthesis. Where the casting mold is a fired material, it may be provided with one or more sections which are joined to form the prosthesis and separated as needed to remove the finished product. However, at least the portions connected to macroporous textured regions of the mold require breakage and special cleaning to separate the finished prosthesis from the mold. As noted above, ultrasonic cleaning and selective etches may be used to remove all residues of the mold from the cast metal prosthesis.

In this manner a prosthesis is produced that has on at least a portion of its exterior an integral, as-east macrotextured surface 14 with macropores 16 having undercut edge profiles 18. No machining or other post-processing operations are required to achieve this intricately textured surface, and complex texture or surface structures are designed directly into the casting mold and created using the three-dimensional printing techniques described herein.

FIGS. 6B and 6C illustrate steps in an alternative process for making a cast implantable prosthetic with a macroporous surface region. In accordance with this alternative process, a plate 45 having macroporous surface features as described in connection with FIGS. 4A, 4B above is placed in a surface recess or receiving region 92 of a molding block 90a or 90b, and the set of molding blocks 90a, 90b are then placed together to form a closed mold cavity 94. The cavity is next filled with wax via injection ports 95 to produce a hybrid preform 96 having a wax body with the texture plates 45 located in the desired regions of their surface. As illustrated, the plates 45 have an "A" side, and a "B" side, the "A" side having a printed macroporous pattern which is the casting-negative or three-dimensional complement of the ultimately intended prosthesis texture pattern.

Once the hybrid wax-plus-plate preform 96 is formed, a refractory investment is formed about it, as described for the first process. Advantageously, the "B" side of plate 45 is also formed with a set of macroscopic surface features. These features need not, however, correspond to trabecular bone growth enhancing or mechanically strong bone coupling patterns, but serve only to assure that the investment couples securely to the back of the plate when building up the investment casting mold. If the plate is formed of a ceramic-forming powder as described above, plate 45 may be green, and may be fired with the investment to result in a unitary ceramic casting mold with interior texture regions. In that case, the texture or surface relief of the "B" side of plate 45 may consist of a generally flat surface with only a small number of posts, hooks, dovetails, or features intended to engage the hardened investment.

The foregoing description of three-dimensional printing of molds or mold parts constitutes a presently preferred method of forming a prosthesis with the desired macroporous surface texture. However, the invention also contemplates that the desired macrotexture may be directly formed on an already-cast bone prosthesis. In that event, the already-cast bone prosthesis is mounted on the work table 21 and the scanning and leveling mechanism 28, 34 is actuated to build up the desired surface features using a sinterable metallic powder and a binder. In this case, the scanner may be programmed, in conjunction with motion of the platen 21 in a vertical direction, to follow the curvature (if any) of the prosthesis. The solidified surface textured pattern is then sintered to fix and strengthen it.

While applicant envisions that the process may be applied using conventional sinterable metal powders, several constraints are to be considered as follows. Preferably the sintering step should not degrade the cast prosthesis. This places a limit on permissible sintering time/temperature cycles. Furthermore, the surface material must be strong and attach well to the existing body. This may require use of titanium or other metal powders that enhance alloy bonding, and may also benefit from microcrystalline or other powders, such as an alloying mixture, that add strength. In general, structure added by powdered metal technology may be expected to have a large degree of shrinkage during sintering. Accordingly, the texture may be applied in small discrete patches to avoid thermal cracking or stress, and the features may be magnified by a scale factor to compensate for shrinkage.

Applicant further contemplates that other portions of a prosthesis may be directly printed in the manner shown for fabrication of the mold of FIG. 3. For example, polymer or plastic components may be built in this fashion onto or into a prosthesis, using appropriate base powders 20, binder and post-processing.

Figure 7:
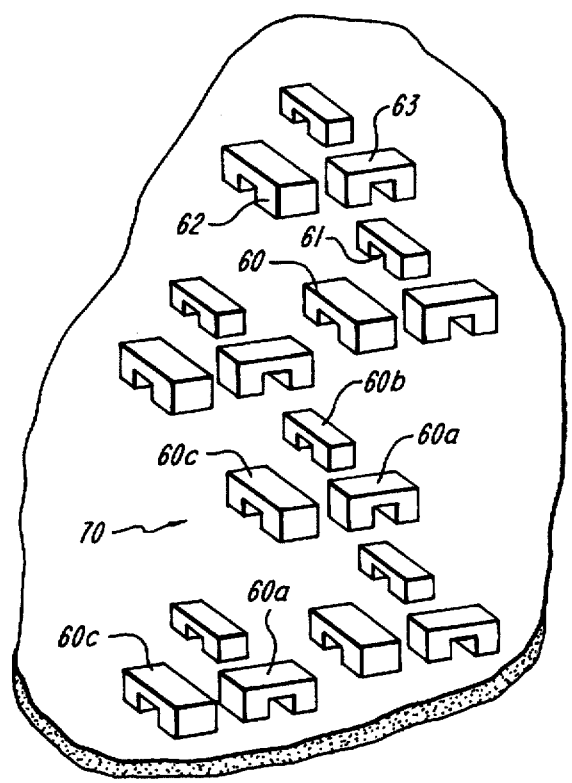
FIG. 7 is a detailed view of one simple undercut surface pattern mold made in accordance with the present invention.

Returning now to the form of suitable macroporous structures, FIG. 7 shows an enlarged and simplified perspective view of one pattern 70 suitable for the surface of the present invention. A plurality of bridges or arches 60 protrude above the nominal surface level. Each bridge 60 has legs 62, a top surface 63 and an underpass 61 that extends all or part way through the surface, and the bridges are closely spaced and elongated in one of several different directions, illustrated by the mutually orthogonal orientations of bridges 60a and 60b, or 60a and 60c. Other arrays of simple or complex anchor structures are possible, in which the bridges are arranged differently, or augmented or replaced by other shapes such as protruding hooks, undercut pits, ridges or the like.

Figure 8:
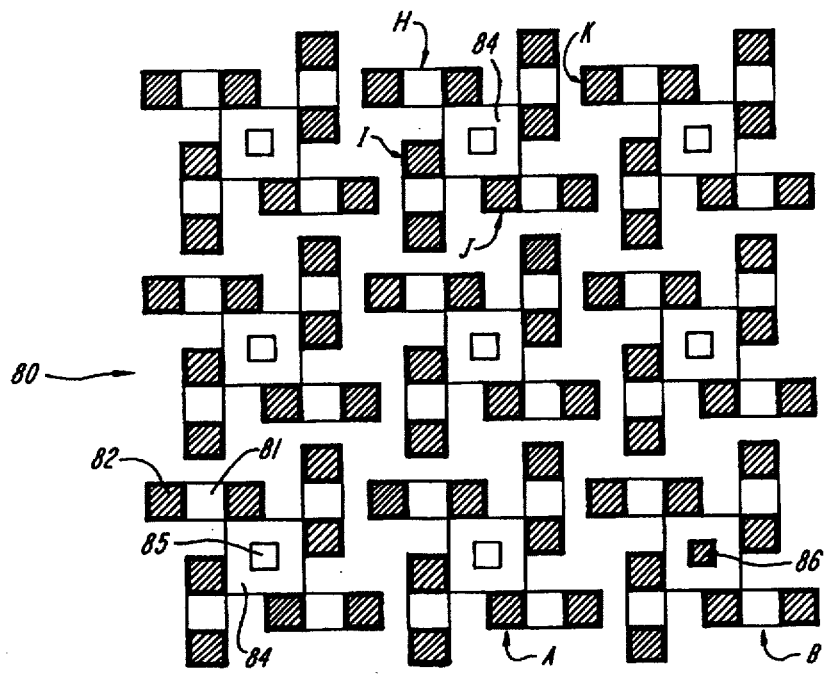
FIG. 8 is a detailed view of an array of undercut surface features forming a macrotextured mold in accordance with the invention.

FIG. 8 illustrates a form of presently preferred texture pattern 80, wherein shaded squares 82 correspond to the legs 62 of FIG. 7, and the unshaded squares 81 between adjacent legs correspond to the undercuts 61 of FIG. 7. In this multiply-repeated pattern, four undercut bridges H, I, J, K are arranged, ann-like, about a central block or platform region 84 which, as shown, is twice as wide as the leg 82, and that in turn has a central dimple 85 or peak 86 extending down or up, respectively, in its center. The shaded legs may, for example, be formed as three-by-three dot binder pattern features by three-dimensional powder consolidation printing using a scan jet with 0.175 mm dot size, with a height of six lines (layers) totaling 1.05 mm, the undercut 81 extending half that height, and the dimple 85 or post 86 being two dots (0.35 mm) square and extending three layers down or up from the nominal center platform 84 which is illustratively half height, (0.52 mm) or three layers tall. The illustrated pattern has greatly interconnected topography, with the through holes or undercut tunnels 81 located to pass under the top surface of the bridge, and adjacent to the vertical face of the central block or platform 84, thus promoting interlocked bone growth along several different planes.

Two variations of this pattern are shown: variation A with a central dimple or pit 85, and variation B with a central peak or post 86. These patterns may alternate, or the surface texture may include regions that comprise entirely one type of regular pattern. It will be noted that this artificial texture is readily susceptible to computerized generation, and may be numerically manipulated or embodied in a simple program to drive a three-dimensional printer so that the pattern is formed sideways or on a rising slanted surface such as the walls 38C of mold 38 (FIG. 3E) formed as minor horizontal variations in pattern contour in each layer of a vertical wall formed as the binder head scans horizontally over successive layers. This pattern and others can be modified to define similar features on a curved surface.

By directly forming the surface pore structure on an article or mold surface as described above, applicant is able to independently optimize structural parameters affecting both bone growth and bone strength, principally by varying the pattern or dimension of macroporous features at different regions of the surface, or even at different levels. As already described, the pore structure preferably has a minimal size or spacing which promotes trabecular tissue growth, and at least some undercut features. The latter prevent bone from pulling out of the surface, hence they enhance tensile strength of the bone-prosthesis interface. The presence of sharply rising or falling pits, ridges or posts of a sufficient size, and regions between for growth of bony complementary shapes, contributes to the shear strength of the interface, preventing in-plane sliding along the junction. Thus, different macrofeatures can maximize shear strength, tensile strength and bone growth.

Using layer by layer scanning to build up a desired three-dimensional relief mold, different features are preferably built up in different regions to optimize these properties. For example, one region may have entirely shear-strength enhancing protuberances to securely fix the prosthesis when it is initially installed, while nearby regions that are to be closely in contact with bone may carry undercut and appropriately sized pores for enhancing the development of high tensile strength new bone growth over time. In this case, the first protuberances offer temporary fixation that allows the second set to grow and eventually become fully integrated.

As clinical use and observation of these new porosity-forming techniques are increased, it may turn out that different sizes or types of porosity are desirable to enhance growth or attachment processes at different depths from the bone-contacting surface. In that event, the above-described techniques enable one to readily form a macroporous three-dimensional mold structure, in which the cast prosthesis acquires a pore structure distribution that varies in pore type or dimension with varying depth from the surface.

The foregoing description of methods of manufacture and illustrative embodiments is presented to indicate the range of constructions to which the invention applies. The invention having overcome numerous drawbacks in the fragility, manufacture and general utility of bone prostheses having complex surface features, variations in the physical architecture and mold processes of the present invention will occur to those skilled in the art, and such variations are considered to be within the scope of the invention in which patent rights are asserted, as set forth in the claims appended hereto.

What is claimed is:

1. A method of making a bone prosthesis, comprising the steps of
   a) providing a predetermined, computer controlled scan actuation pattern suitable to yield a casting mold having formed therein a macrotextured surface having macropores with undercut edge profiles in selected regions thereof;

b) depositing a layer of a ceramic-forming powder material in a confined region;

c) applying a binder material to the ceramic-forming powder material in selected regions of the layer, according to the predetermined scan actuation pattern, to solidify the ceramic-forming powder material in the selected regions;

d) repeating steps (b) and (c) a predetermined number of times to deposit successive layers of ceramic-forming powder, with variations in regions to which binder material is applied such that a solidified portion of each layer is bonded to a preceding layer, to form a casting mold that defines a negative of the bone prosthesis, at least a portion of the casting mold having a textured surface including macropores with undercut edge profiles corresponding to the variations of said regions;

e) removing loose ceramic-forming powder material from the casting mold;

f) casting a material in contact with the casting mold and hardening the material to form a bone prosthesis; and g) removing the bone prosthesis from the casting mold, whereby the bone prosthesis has an as-cast macro textured surface characterized by macropores with undercut edge profiles on at least a portion of its exterior.

2. The method of claim 1 wherein the powder material is a ceramic forming material selected from the group consisting of alumina, beryllia, silica, silicon carbide, zirconia and mixtures thereof.

3. The method of claim 1 wherein the binder material comprises an organic or inorganic binder material selected from the group consisting of aqueous colloidal silica, alcohol-based colloidal silica, cellulosic resins, butyral resins, polycarbosilazane, silicate-based materials, alcohol based binders, and alkyd-based binders.

4. The method of claim 1 where the binder material comprises aqueous colloidal silica.

5. The method of claim 1 further comprising the step of removing non-bonded ceramic-forming powder and firing the casting mold to yield a ceramic material.

6. The method of claim 1 wherein the molten metal is a metal alloy.

7. The method of claim 1 further wherein the step of removing the bone prosthesis from the casting mold includes destroying the casting mold.

8. A method of making a bone prosthesis comprising the steps of:

providing a predetermined, computer controlled scan actuation pattern suitable to yield a casting mold having formed therein a macrotextured surface having macropores with undercut edge profiles in selected regions thereof;

applying a three-dimensional printing process to form a green casting mold by successive applications of a binder material to a ceramic forming powder according to the predetermined scan actuation pattern, to bond at least some of the powder together into a solid body forming said green casting mold, at least a portion of the green casting mold having a macroporous textured surface including macropores with undercut edge profiles;

removing non-bonded powder material from the green casting mold;

firing the green casting mold to yield a ceramic casting mold;

casting a molten metal against the ceramic casting mold and allowing the molten metal to harden in contact with the casting mold to form the bone prosthesis, at least a portion of the bone prosthesis thereby having an as-cast macrotextured surface including macropores with undercut edge profiles; and separating the bone prosthesis from the casting mold.

9. The method of claim 8, wherein the green casting mold comprises a plate, and the process further comprises the steps of attaching the plate to a wax form;

forming an investment about the plate and form; and firing the plate and investment to yield said ceramic casting mold.

* * * * *